United States Patent [19]
Bertina et al.

[11] Patent Number: 6,043,035
[45] Date of Patent: Mar. 28, 2000

[54] METHOD FOR DETERMINING A RISK FACTOR FOR THROMBOSIS

[75] Inventors: Rogier Maria Bertina, HB Leiden; Pieter Hendrick Reitsma, CH Leiden; Swibertus Rudolfus Poort, BM Leiden; Frits Richard Rosendaal, KC Wassenaar, all of Netherlands

[73] Assignee: Rijks University Leiden, Leiden, Netherlands

[21] Appl. No.: 08/962,790

[22] Filed: Nov. 3, 1997

[51] Int. Cl.[7] .............................. C12Q 1/68; C12P 19/34; C07H 21/04

[52] U.S. Cl. ............................ 435/6; 435/91.2; 536/23.1; 536/24.33

[58] Field of Search ................. 435/6, 91.2; 536/23.1

[56] References Cited

PUBLICATIONS

S.J.F. Degen et al., *Biochemistry*, 26:6165–6177, 1987.
S.R. Poort et al., *Blood*, 88:10:3698–3703, 1996.
S.R. Poort et al., *Thromb Haemost*, 78:1157–63, 1997.
S.R. Poort et al. *Thrombosis and Haemostasis*, 72(6):819–24, 1994.
Margaglione et al. Ann. Intern. Med.; vol. 129, pp. 89–93, 1998.
Reuner et al. Stroke, vol. 29, pp. 1765–1769, 1998.

*Primary Examiner*—Lisa B. Arthur
*Assistant Examiner*—Jehanne Souaya
*Attorney, Agent, or Firm*—Gregory R. Muir; Mary E. Gormley

[57] ABSTRACT

A method for determining whether an individual is at increased risk for thrombosis, comprising detecting the presence or absence of a genetic mutation located in the 3' untanslated region of the prothrombin gene (G to A mutation at position 20210) that is correlated with elevated prothrombin levels in individuals with the mutation, wherein the elevated prothrombin levels are associated with increased risk for thrombosis. Also provided are kits and primers that specifically hybridize adjacent to the region of the prothrombin gene that contains the G to A mutation at position 20210.

18 Claims, 3 Drawing Sheets

SEQUENCE LISTING

<160> NUMBER OF SEQ ID NOS: 8

<210> SEQ ID NO 1
<211> LENGTH: 20
<212> TYPE: DNA
<213> ORGANISM: human

<400> SEQUENCE: 1
tctagaaaca gttgcctggc                                           20

<210> SEQ ID NO 2
<211> LENGTH: 22
<212> TYPE: DNA
<213> ORGANISM: human

<400> SEQUENCE: 2
atagcactgg gagcattgaa gc                                        22

<210> SEQ ID NO 3
<211> LENGTH: 11
<212> TYPE: DNA
<213> ORGANISM: human

<400> SEQUENCE: 3
gcragcctca a                                                    11

<210> SEQ ID NO 4
<211> LENGTH: 8
<212> TYPE: DNA
<213> ORGANISM: human

<400> SEQUENCE: 4 tcgaagtt                                                         8

<210> SEQ ID NO 5
<211> LENGTH: 10
<212> TYPE: DNA
<213> ORGANISM: human

<400> SEQUENCE: 5
gcgagcttca                                                      10

<210> SEQ ID NO 6
<211> LENGTH: 10
<212> TYPE: DNA
<213> ORGANISM: human

<400> SEQUENCE: 6
cgctcgaagt                                                      10

<210> SEQ ID NO 7
<211> LENGTH: 10
<212> TYPE: DNA
<213> ORGANISM: human

<400> SEQUENCE: 7
gcaagcttca                                                      10

<210> SEQ ID NO 8
<211> LENGTH: 10
<212> TYPE: DNA
<213> ORGANISM: human

-continued

<400> SEQUENCE: 8
cgttcgaagt                                                                                                    10

METHOD FOR DETERMINING A RISK FACTOR FOR THROMBOSIS

BACKGROUND OF THE INVENTION

1. Field of the Invention

The present invention relates to the field of haemostasis and in particular to the aspect of thrombosis. More particularly the invention is directed at a method for screening and diagnosis of thrombophilia, especially hereditary thrombophilia. The method according to the invention can then be used for determining the risk for thrombosis in individuals.

2. Description of the Related Art

Thrombosis is a principal human affliction, killing hundreds of thousands and debilitating millions each year by myocardial infarction, pulmonary embolism, or stroke. Risk factors include both hereditary and acquired conditions. Generally, a tendency towards thrombosis could arise from hyperactive coagulation pathways, hypoactive anticoagulant mechanisms, or hypoactive fibrinolysis. Mutations in genes that encode proteins in these pathways play an important role in the predisposition to thrombosis. Variant alleles of the genes encoding protein C, protein S, antithrombin, and fibrinogen have been shown to be relatively strong, but uncommon risk factors for thrombosis. Genetic analysis of these genes showed a large heterogeneity of mutations. More recently, a poor anticoagulant response of plasma to activated protein C (APC) due to the presence of a mutant factor V molecule (factor V R506Q, factor V Leiden) was discovered and is as yet the most common hereditary risk factor for thrombosis known. Recently some support was obtained for the hypothesis that the clustering of thrombosis in families is due to epistatic effects. Studies in selected families with venous thrombosis indicated that the presence of mutations in two genes may increase the penetrance of the thrombotic disease.

The discovery of genetic risk factors for thrombosis came after the identification of families in whom the thrombophilia segregated with an abnormal result in a plasma test (protein C, protein S, antithrombin, and APC resistance). However, despite the ever growing insight into the processes of coagulation and fibrinolysis, the underlying cause of many inherited thrombotic events remained unsolved.

The serine protease thrombin, formed by cleavage of human prothrombin, exerts a central action to the processes of thrombosis and haemostasis. The thrombin molecule plays a role in the final stage of blood coagulation: the formation of an insoluble fibrin clot. The hitherto known congenital disorders of prothrombin are rare and involve either reduced synthesis of an (ab)normal molecule (referred to as hypoprothrombinemia or type I prothrombin deficiency) or the normal synthesis of a dysfunctional molecule (referred to as dysprothrombinemia or type II prothrombin deficiency). Homozygous patients with hypoprothrombinemia generally have plasma prothrombin levels between 1% and 25% of normal values, conditions that are usually associated with a clinical bleeding tendency. Heterozygous patients, in contrast, have prothrombin levels of about 50% and at worst very mild bleeding problems. Patients with dysprothrombinemia have only 2% to 50% of the clotting activity of normal prothrombin; in these patients the severity of the bleedings correlates fairly well with the amount of prothrombin activity in plasma. A number of dysprothrombinemias have been further characterized by amino acid sequence analysis of the isolated prothrombin molecule or, more recently, a few hypo- and dysprothrombinemias by nucleotide sequence analysis of their prothrombin genes. In one example DNA sequence analysis revealed homozygosity for a single basepair (bp) transition in exon 3 at position 1305 (A to G) that predicts the replacement of tyrosine for cysteine at amino acid residue 44 of the mature protein. This mutation in exon 3 of the prothrombin gene is associated with a bleeding tendency and can therefore not be the underlying cause of many unexplained thrombotic events.

SUMMARY OF THE INVENTION

The present invention reveals that elevated levels of prothrombin are a hithereto unrecognized risk factor for thrombosis. The nature of a common cause of such elevated levels was also established and found to be a genetic variation in the prothrombin gene at position 20210 (Blood, vol. 88 no. 10, 1996; pp 3698–3703).

In one aspect the present invention provides a method for determining a risk factor for thrombosis comprising the assessment whether prothrombin levels in an individual are elevated. This assessment can be performed by measuring the protrombin levels in a suitable sample and comparing this level with normal prothrombin values. It may also be assessed by determining the presence or absence of a genetic element which is correlated with elevated prothrombin levels. In particular, the invention provides such a method in which said genetic element is a mutation in the prothrombin gene, more particularly a mutation at nucleotide position 20210 of the prothrombin gene.

In another aspect the present invention provides a kit for use in said method. The present invention also provides a nucleotide sequence comprising at least part of the nucleotide sequence of the human prothrombin gene, wherein nucleotide G at position 20210 is replaced by A, as well as the use of such a sequence for the detection of such a mutation. The present invention also provides primers for the allele specific detection of a mutation of the prothrombine gene at position 20210.

DETAILED DESCRIPTION OF THE INVENTION

Prothrombin is the precursor of the serine protease thrombin, a key enzyme in the processes of hemostasis and thrombosis, that exhibits procoagulant, anticoagulant, and antifibrinolytic activities. It was hithereto unrecognized that elevated levels of prothrombin are a risk factor for thrombosis. With the present invention such a correlation has now been established. As exemplified in example 1, the prothrombin level can be measured in a human plasma sample using techniques known in the art. A normal value can be derived by measuring prothrombin levels in a statistically sufficient number of healthy individuals.

Prothrombin levels may also be assessed by detecting whether a genetic element which is correlated with elevated prothrombin levels is present or absent in a suitable sample, such as a human blood sample. Said genetic elements may be identified by methods known in the art as exemplified in example 2. One possible strategy that may be employed to identify said genetic elements is straightforward and encompasses the steps of sequencing a candidate gene in a panel of probands from families with documented thrombophilia, followed by estimating the risk factor for thrombosis associated with any observed sequence variation in a population based patient-control study.

By the term "genetic element", any nucleotide sequence present in the genome of the organism under investigation is meant. Genetic elements correlated with elevated prothrombin levels comprise nucleotide sequences from the prothrombin gene itself as well as from any other gene which might cause elevated prothrombin levels. Abberations in those genes may be caused by deletions, insertions, mutations, chromosomal dislocations or other genetic mechanisms.

Here, as a candidate gene, the prothrombin gene was analysed in a search for genetic elements that may contribute to elevated levels of prothrombin and/or thrombosis. Prothrombin is encoded by a 21-kb-long gene localized on chromosome 11, position 11p11-q12. The prothrombin gene is organized in 14 exons, of which exon 1 comprises the 5' untranslated (UT) region and exon 14 comprises the 3'-UT region. Regions flanking the gene either upstream or downstream may play regulatory roles in gene expression and were therefore included in the analysis. The nucleotide sequence of the prothrombin gene, its flanking sequences as well as the position of the various exons has been described previously (Biochemistry 26, 6165–6177, 1987).

Genetic analysis of the prothrombin gene comprises selective nucleic acid amplification of all of the exons including the 5'- and 3'-UT regions of the gene as well as other regulatory elements of the gene.

Various techniques for amplifying nucleic acid are known in the art. One example of a technique for the amplification of a DNA target segment is the so-called "polymerase chain reaction" (PCR). With the PCR technique the copy number of a particular target segment is increased exponentially with a number of cycles. A pair of primers is used and in each cycle a DNA primer is annealed to the 3' side of each of the two strands of the doubled stranded DNA-target sequence. The primers are extended with a DNA polymerase in the presence of the various mononucleotides to generate double stranded DNA again. The strands of the double stranded DNA are separated from each other by thermal denaturation and each strand serves as a template for primer annealing and subsequent elongation in a following cycle. The PCR method has been described in Saiki et al., Science 239, 487, 1988 and in European Patents no. EP 200 362 and EP 201 184.

Another technique for the amplification of nucleic acid is the so-called transcription based amplification system (TAS). The TAS method is described in International Patent Appl. no. WO 88/10315. Transcription based amplification techniques usually comprise treating target nucleic acid with two oligonucleotides, one of which comprises a promotor sequence, to generate a template including a functional promotor. Multiple copies of RNA are transcribed from said template, which can serve as a basis for further amplification.

An isothermal continuous transcription based amplification method is the so-called NASBA process as described in European Patent no. 329 822. NASBA includes the use of T7 RNA polymerase to transcribe multiple copies of RNA from a template including a T7 promotor. Other amplification techniques include the Ligase Chain Reaction (LCR) and the Repair Chain Reaction (RCR).

The term "oligonucleotide" as used herein refers to a molecule comprising two or more deoxyribonucleotides or ribonucleotides. These oligonucleotides may function as primers and probes.

The term "primer" as used herein refers to an oligonucleotide either naturally occurring (e.g. as a restriction fragment) or produced synthetically, which may act as a point of initiation of synthesis of a primer extension product and which is able to hybridize to a nucleic acid strand (template or target sequence) when placed under suitable conditions (e.g. buffer, salt temperature and pH) in the presence of nucleotides and an agent for nucleic acid polymerization, such as DNA dependent or RNA dependent polymerase. A primer must be sufficiently long to prime the synthesis of extension products in the presence of an agent for polymerization. A typical primer contains at least about 10 nucleotides in length of a sequence substantially complementary or homologous to the target sequence, but somewhat longer primers are preferred. Usually primers contain about 15–26 nucleotides, but longer primers may also be employed. Normally a set of primers will consist of at least two primers, one 'upstream' and one 'downstream' primer which together define the amplificate (the sequence that will be amplified using said primers). The primers used for amplification of the various regions of the prothrombin gene were synthesized by the methoxyphosphoramidite method (Tetrahydron Letters 22, 1859–1865, 1981). The sequences of the primers were chosen such that they flank the target regions of the prothrombin gene. Suitable primers for amplification of the various transcribed and untranscribed regions of the human prothrombin gene are those listed previously (Thrombosis and Haemostasis 78, 1157–1163, 1997; Thrombosis and Haemostasis 72, 819–824, 1994).

Detection of mutations may, inter alia, be performed by direct sequence analysis of amplified nucleic acid, by allele specific amplification or by restriction fragment analysis. It may also be performed by hybridisation with a probe which is able to hybridize to the amplified stretch of nucleic acid material.

The term "probe" refers to an oligonucleotide, typically labeled, that forms a duplex structure with a sequence of a target nucleic acid due to complementary base pairing. The probe will comprise a hybridizing region, preferably consisting of 10 to 50 nucleotides, more preferably 20 to 30 nucleotides, corresponding to a region of the target sequence. The hybridizing region of a probe is preferably identical or fully complementary to the sequence of the target region. The hybridizing region may also contain a certain number of mismatches, those skilled in the art of nucleic acid technology can determine duplex stability considering a number of variables including the length and base-pair composition of the probe, ionic strength of the buffer, reaction temperature and incidence of mismatched base pairs, see, e.g. Sambrook et al., Molecular cloning: A laboratory manual, second edition (1989) Cold Spring Harbor Laboratory Press.

The term "label" as used herein refers to any atom or molecule which can be attached to a nucleic acid and which can be used either to provide a detectable signal or to interact with a second molecule to modify the detectable signal provided by said second molecule. Prefered labels are (non)-metal sol particles, radioisotopes fluorescent compounds, enzymes or (electro)chemoluminescent compounds.

Hybridisation of the probe with the target sequence may be detected by techniques known in the art of nucleic acid technology such as Northern or Southern blotting, see e.g. Sambrook et al., supra. Prefered analysis systems are electrochemiluminescence (ECL) based analysis or enzyme linked gel assay (ELGA) based analysis.

Sequence analysis includes direct analysis of the DNA sequence flanking and constituting the exons and untranslated regions of the prothrombin gene. This method involves any protocol that is currently available to any person skilled in the art for directly determining DNA- or RNA sequences, such as the didesoxynucleotide method described by Sanger (Proc. Natl. Acad. Sci. USA, 74 5463–7, 1977).

It is also possible to analyse the amplified material through restriction fragment analysis. In this method the amplified material is digested with restriction enzymes that recognize DNA sequences that are either present in DNA sequences derived from patients carrying a mutation in the exons or untranslated regions of the prothrombin gene, or that are present in the native sequence encoding prothrombin.

It is also possible to analyse a known mutation by allele specific amplification (Trends in Genetics, 12, 391–392, 1996 and Mullis et al. eds, The polymerase chain reaction, Birkhauser, Boston, Basel, Berlin, 1994, pp1–13) Allele specific PCR for the prothrombin 20210 A variation has been described in Thrombosis and Haemostasis 78, 1157–1163 (1997). This technique is based on the observation that under certain conditions primer elongation cannot take place when the 3' terminal nucleotide of a primer is not complementary to the template. With the use of two forward primers that differ only at their terminal 3' nucleotide it is possible to distinguish between homozygous or heterozygous individuals, for instance with respect to their Prothrombine 20210 alleles: analysis of material from homozygous individuals will result in a positive amplification result with either one of the primers, material from heterozygous individuals will result in a positive amplification with both primers.

As is illustrated in example 2 a specific mutation in the prothrombin gene has been demonstrated that is representative for a group of patients exhibiting thrombophilia without the cause thereof having been previously determined. Example 2 provides details on the detection of mutations at nucleotide position 20210 of the prothrombin gene and illustrates the general use of the methods for the detection of mutations in the prothrombin gene.

The study shown in example 2 shows that a novel sequence variation in the prothrombin gene (nt 20210 G to A) is a moderate risk factor for venous thrombosis (odds ratio: 2.8; 95% confidence interval: 1.4 to 5.6). The further observations that the 20210 A allele is associated with elevated prothrombin levels, that carriers of this allele have significantly higher prothrombin levels than non-carriers, and that elevated plasma prothrombin itself is also a risk factor for thrombosis indicates that the 20210 A allele acts through the elevated prothrombin levels.

This study does not show the mechanism(s) by which the 20210 A allele of the prothrombin gene may contribute to higher prothrombin levels. The association found for these two variables (Table 3) and the location of 20210 G to A transition in the 3'-UT region of the prothrombin gene may indicate a higher efficiency of polyadenylation, a relatively higher translation efficiency or higher stability of the transcribed mRNA. The G/A sequence variation is located at the last position of the 3"-UT at or near the cleavage site in the mRNA precursor to which poly A is added. Three conserved sequences in mRNA precursors, located in the vicinity of this site, are required for cleavage and polyadenylation: the AAUAAA sequence, the nucleotide to which poly A is added, and the region downstream of this nucleotide. Generally, the nucleotide to which poly A is added is an A, mostly preceded by a C. As a consequence of the G to A transition at position 20210, a CA dinucleotide (instead of GA) has been introduced at or near the cleavage and polyadenylation site. However, in vitro experiments so far do not support a hypothesis in which this nucleotide substitution will result in an increased efficiency of the 3' end formation.

EXAMPLE 1

Subjects.

Patients came from a population-based case-control study on venous thrombosis, the Leiden Thrombophilia Study (LETS) (Lancet 342, 1503, 1993). Briefly, patients were selected from the computer files of the Anticoagulation Clinics in Leiden, Amsterdam and Rotterdam. In the Netherlands, Anticoagulation Clinics monitor coumarin treatment in virtually all patients with venous thrombosis in a defined geographic area. Included are 474 unselected and consecutive outpatients younger than 70 years of age who were referred for anticoagulant treatment because of a first objectively diagnosed episode of deep-vein thrombosis. The median time between the occurrence of the deep-vein thrombosis and blood collection was 19 months (range: 6 to 68 months). Ninety-one percent of the eligible patients were willing to take part in the study. The thrombotic patients were asked to find their own healthy control subject according to predefined criteria, as used in the LETS. This resulted in 474 population control subjects matched for age and sex. The mean age for patients and controls was 47 years (range: 16 to 70 years for patients; range: 16 to 73 years for controls) and the male/female ratio among patients and controls alike was ¾.

Materials

The chromogenic substrate S-2238 was obtained from Chromogenix (Mölndal, Sweden). The Echis carinatus venom was obtained from Sigma (Sigma Chemical, St Louis). All other chemicals were of analytical grade from Merck (Darmstadt, Germany).

Blood Collection and Laboratory Analysis.

Blood was collected in tubes containing 0.106 mmol/l trisodium citrate. Plasmas were prepared by centrifugation for 10 minutes at 2,000 g at room temperature and stored at −70° C. in 1.5-ml aliquots.

Prothrombin activity was measured with a chromogenic method using S-2238 as a substrate and Echis carinatus venom as activator. Prothrombin antigen was determined using Laurell electroimmunoassay. Protein C avtivity was measured with Coamate protein C (Chromogenix, Mölndal, Sweden). An amidolytic heparin cofactor assay (Chromogenix) was used for antithrombin activity measurements. Total protein S antigen was determined by polyclonal enzyme-linked immunosorbent assay (ELISA). The results are expressed in units per milliliter, in which 1 U refers to the activity or antigen present in 1 ml of pooled normal plasma.

Statistical Analysis

Odds ratios (ORs) were calculated as a measure of relative risk in the standard unmatched fashion. A 95% confidence interval (CI) was constructed according to Woolf (Am. J. Hum. Genet. 19, 251, 1955). Generally, the OR estimates the risk of thrombosis when a risk factor is present relative to the reference category. For risk factor analysis concerning plasma prothrombin values, 48 patients using oral anticoagulant therapy were excluded from the LETS group. To assess a dose-response relation, the prothrombin values of both patients and controls were stratified into quartiles and the ORs calculated for the three higher levels relative to the lowest reference level. Adjustment for current oral contraceptive use (yes/no), body mass index (in kilograms per square meter), menopause (yes/no), smoking (yes/no), age and sex was performed by unconditional logistic regression. Effect modification was assessed by stratified analysis and logistic regression with interaction terms.

Results

Prothrombin levels were determined in 900 plasma samples, 426 from patients as described above with those (n=48) on oral anticoagulant treatment excluded, and 474 from normal age and sex matched controls. To assess to what extent an increased prothrombin level is a risk factor for venous thrombosis, we stratified the prothrombin levels of patients and control subjects into quartiles (Table 1).

TABLE 1

Thrombosis Risk for Plasma Prothrombin Levels

| Prothrombin Activity (U/ml) | No. of Patients* (n = 426) (%) | No. of Controls (n = 474) (%) | Total No. (n = 900) (%) | OR*** | 95% CI |
|---|---|---|---|---|---|
| <0.95 | 85 (20) | 134 (28) | 219 (24) | 1.0** | |
| 0.95–1.04 | 107 (25) | 125 (26) | 232 (26) | 1.3 | 0.9–2.0 |
| 1.05–1.15 | 102 (24) | 118 (25) | 220 (24) | 1.4 | 0.9–2.0 |
| >1.15 | 132 (31) | 97 (20) | 229 (25) | 2.1 | 1.5–3.1 |

*Patients on oral anticoagulant treatment are excluded (n = 48)
**Reference category
***Test for trend, P < .001

The OR increased with increasing prothrombin levels: subjects with a prothrombin level of greater than 1.15 U/ml had a 2.1-fold higher risk than those in the reference category (<0.95 U/ml). The high-risk stratum of greater than 1.15 U prothrombin/ml comprised no less than 31% of the patients and 20% of the control subjects. It is concluded that a risk factor for thrombosis can be determined by assessing the plasma prothrombin level and comparing this with normal plasma prothrombin levels.

EXAMPLE 2

Subjects.

28 families were randomly selected from a previous study (Thrombosis and Haemostasis 62, 673, 1989) wherein detailed information on the occurrence of venous thromboembolic events was collected. For selection the following criteria were used: (1) apart from the proband, there should be at least two symptomatic (preferentially first degree) relatives; and (2) in probands and symptomatic relatives, deficiences of protein C, protein S, antithrombin, or plasminogen or dysfibrinogenemia were excluded. On average each proband had 2.4 (range: 1 to 6) symptomatic first degree relatives and 1.8 (range: 0 to 5) symptomatic second degree relatives. It was recently estblished by DNA analysis that, in this panel of probands, the frequency of the factor V Leiden mutation (Nature 369, 94, 1994), which is associated with a poor anticoagulant response to APC, is 40%.

Materials

Deoxynucleotides, dideoxynucleotides, and bovine serum albumin were purchased from Pharmacia (Uppsala, Sweden). (alpha $^{35}$-S) dATP (>1,000 Ci/mmol) was obtained from Amersham International (Amersham, UK). Klenow DNA polymerase was from Boehringer Mannheim (Mannheim, Germany). Taq-DNA polymerase (Amplitaq) was purchased from Perkin Elmer-Cetus (Norwalk, Conn.). Restriction enzymes were obtained from New England Biolabs (Beverley, Mass.). Oligonucleotides were synthesized on a Cyclone DNA synthesizer (Millipore, Bedford, Conn.). All other chemicals were of analytical grade from Merck (Darmstadt, Germany).

Blood Collection and Identification of Sequence Variations in the Prothrombin Gene Blood was collected as described in example 1. High molecular weight DNA was extracted from the white blood cell fraction using standard methods.

For the identification of a genetic abnormality (or abnormalities) in the prothrombin gene in DNA from 28 probands with a family history of deep vein thrombosis, the PCR technique was used followed by direct sequencing (Thrombosis and Haemostasis 72, 819, 1994). These sequences were compared with those of 5 healthy control individuals. Genomic DNA was specifically amplified for the 14 exons of the prothrombin gene including the 5'- and 3'-UT regions and their flanking regions using PCR. The primers used in the PCR were derived from the sequence of the gene (Biochemistry 26, 6165, 1987) and are identical to those used in a previous study (Thrombosis and Haemostasis 72, 819, 1994). The fragments obtained by PCR were purified on 1% ultralow melting temperature agarose gel. The segment of the gel containing the amplified segment was excised and sequenced with the appropriate primers using the dideoxynucleotide chain termination method as described by Sanger. Sequencing reactions were electrophoresed on 40 cm long 8% polyacrylamide gels. The gels were dried on Whatman 3 mm paper (Whatman, Maidstone, UK) and exposed to an X-ray film. Genetic abnormalities identified by sequencing were confirmed by restriction enzyme digestion of amplified gene fragments. When the abnormality did not create or abolish a restriction site, such a site was created by introducing a nucleotide substitution with a mutant oligonucleotide during amplification (Blood 80, 2092, 1992). The mutant oligonucleotide was designed with a nucleotide substitution close to the 3' end, such that the combination of the nucleotide substitution and the genetic abnormality created a new restriction enzyme cleavage site.

Genetic analysis of the factor V Leiden mutation (1691 G to A) was performed as previously described (Nature 369, 64, 1994).

Statistical Analysis

Statistical analysis was performed as described in example 1.

Results

Figure 1:
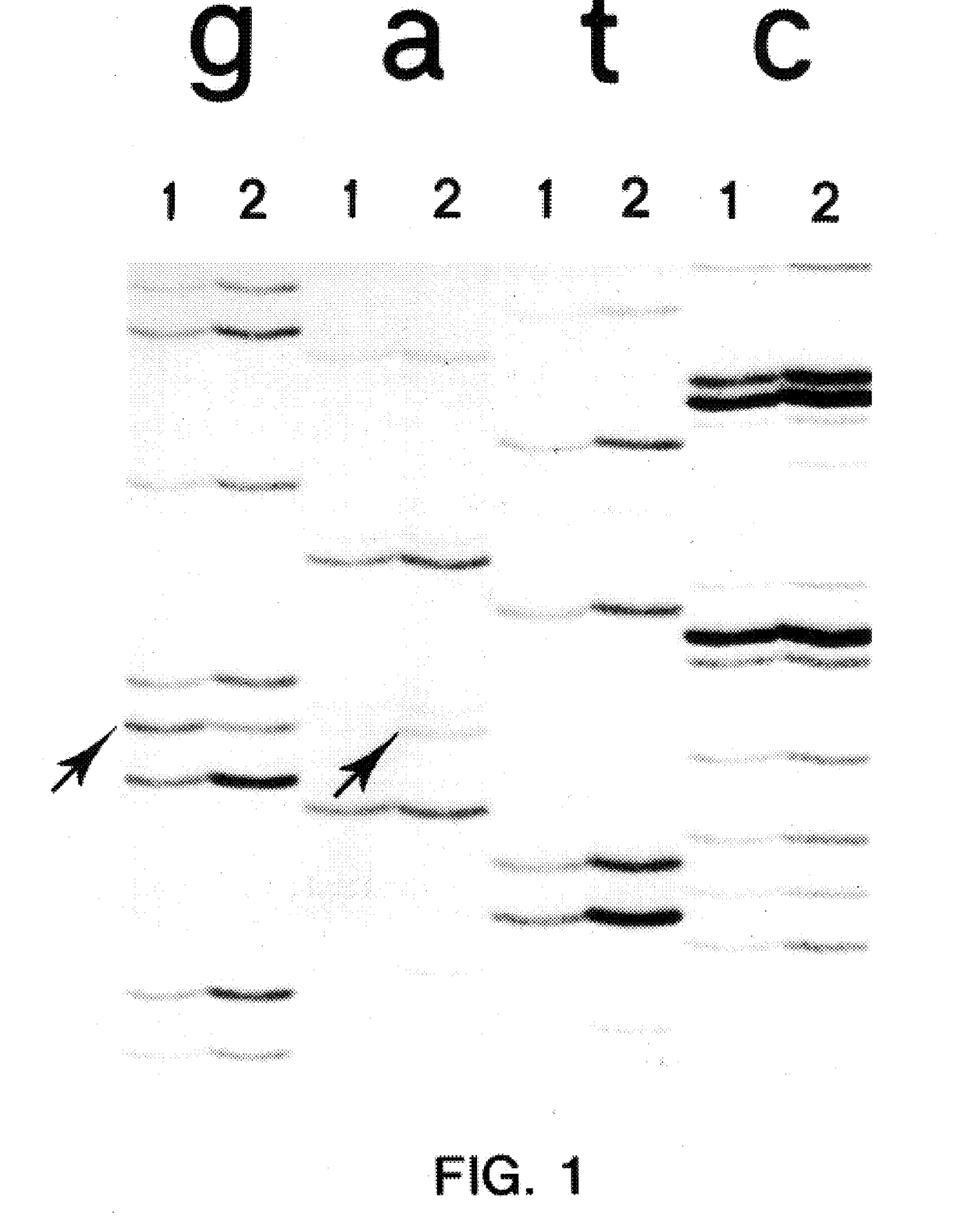
FIG. 1 shows the direct sequencing of the G to A transition at position 20210 in the prothrombin gene of a proband with venous thrombosis.
Figure 2:
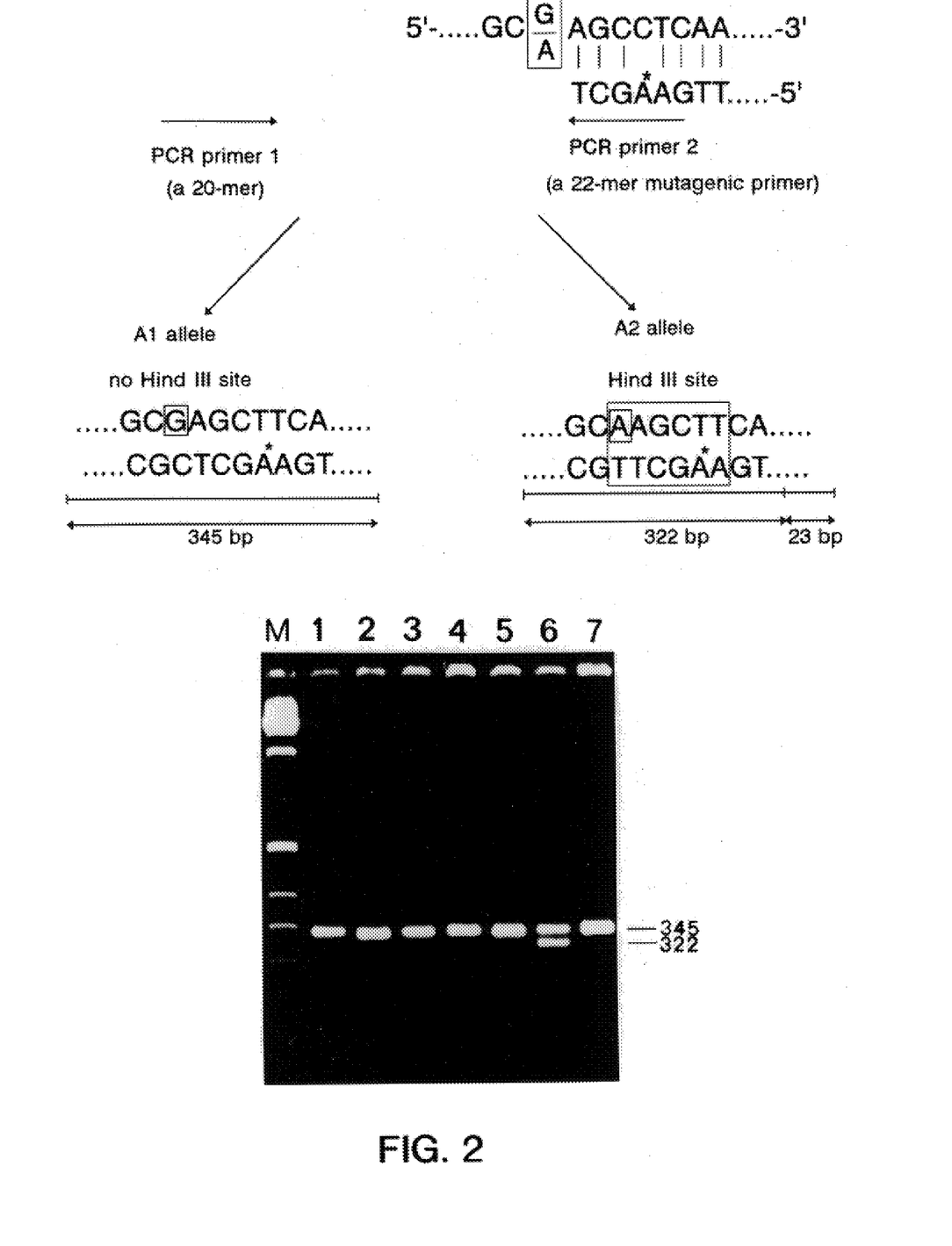
FIG. 2 is an illustration of the strategy for the direct detection of the 20210 A allele in the prothrombin gene.
Figure 3:
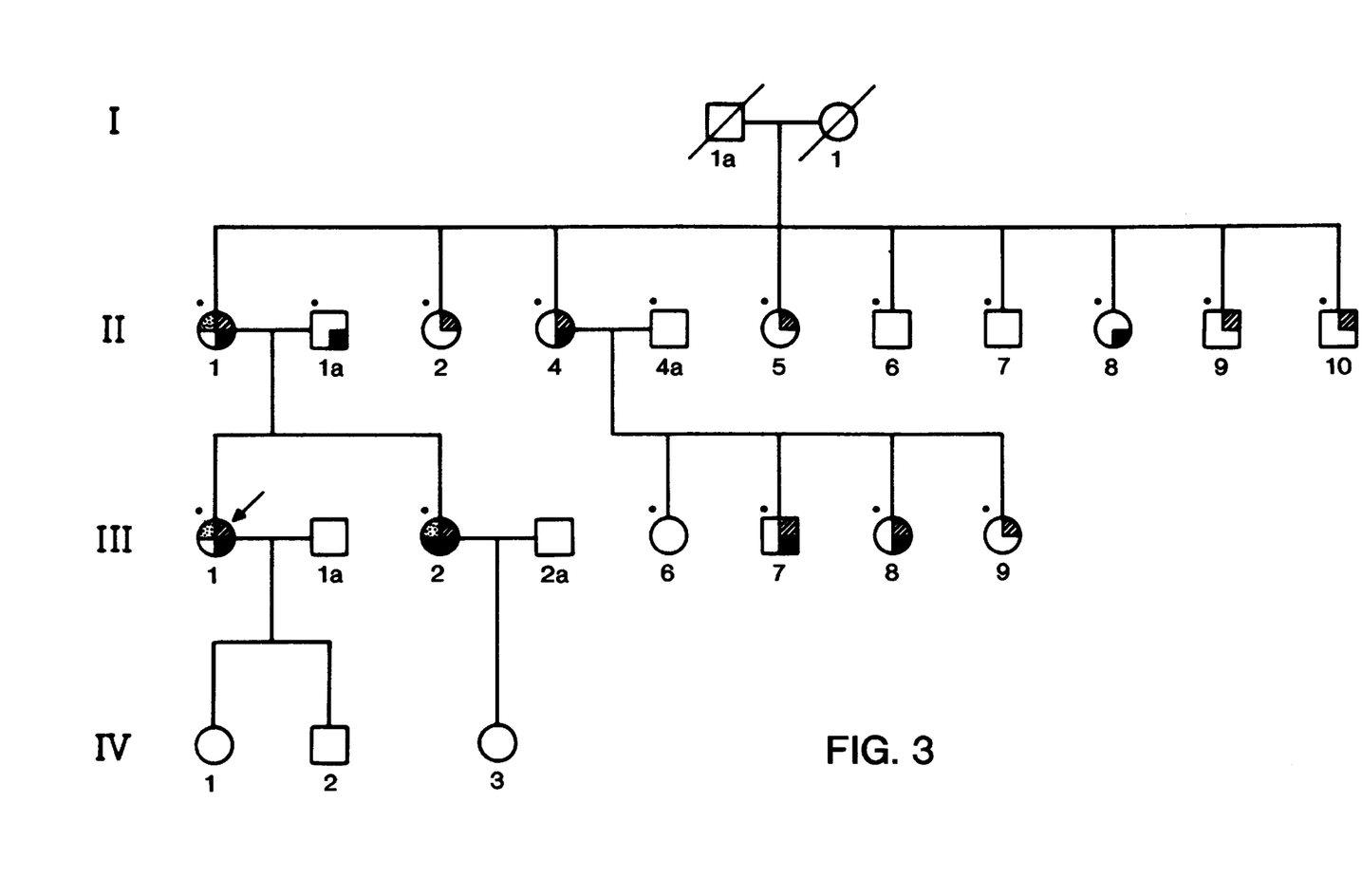
FIG. 3 illustrates the pedigree of a family in whom both the 20210 G/A sequence variation in the prothrombin gene and the factor V Leiden mutation (1691 G/A) are segregating

In the products amplified from genomic DNA of the 28 probands and 5 healthy controls, no nucleotide change was found in the 14 exons and the 5' UT-region of the prothrombin gene, except for sequence variations known as neutral polymorphisms. Only one heterozygous nucleotide transition (G to A) at position 20210, the last nucleotide of the 3' UT-region, was found in DNA of 5 of the 28 probands (18%), but not in DNA of the 5 healthy control individuals (FIG. 1). The presence of this sequence variation was confirmed with restriction enzyme analysis using one mutagenic primer (FIG. 2). In an extended analysis of 100 healthy subjects, the heterozygous state (20210 AG) was detected in 1%. Homozygous (20210 AA) carriers were absent. FIG. 3 shows the pedigree of the family of one of the five thrombophilic patients carrying the variant prothrombin allele. Both the parents of the proband are heterozygous for the 20210 A allele, whereas her sister is homozygous. Interestingly, both the variant prothrombin allele and the factor V Leiden allele segregate in this pedigree. All individuals that experienced a thrombotic event (or events) (II, 1; III, 1; III, 2) carry both genetic defects, wheres all carriers of a single defect are still symptom free. The high frequency (18%) of the 20210 A allele among patients with thrombophilia is probably affected by selection.

The population described in example 1 (LETS) (Lancet 342, 1503, 1993) was analysed for the presence of the Prothrombine 20210 mutation. The prevalence of carriers of the 20210 A allele among healthy control subjects in the LETS was 2.3%, which corresponds to an allele frequency of 1.2% (95% CI: 0.5% to 1.8%). Table 2 shows a higher prevalence of the 20210 AG genotype among patients (6.2%) than among control subjects (2.3%).

TABLE 2

Frequencies and Thrombotic Risk for the 20210 G/A Genotypes in the Prothrombin Gene

| Genotype (nt 20210) | No. of Patients (%) | No. of Controls (%) | ORcrude* | 95% CI |
|---|---|---|---|---|
| GG | 442 (93.8) | 463 (97.7) | 1.0** | |
| AG | 29 (6.2) | 11 (2.3) | 2.8 | 1.4–5.6 |
| AA | — | — | | |

*Adjustment for age and sex, current oral contraceptive use (yes/no), body mass index, in menopause (yes/no) and smoking (yes/no) did not affect these results.
**Reference category.

Homozygous carriers were not found (expected prevalence 0.014%). The relative risk for thrombosis associated with the 20210 A allele was 2.8% (95% CI: 1.4 to 5.6). This association persisted when controlling for age, sex, current pill use, body mass index, menopause and smoking. The 20210 A allele was associated with an increased risk for thrombosis both in men and women. It was also found that the 20210 A allele increased the risk for all age groups. The increased risk (2.8) associated with the 20210 A allele was not the result of overrepresentation of other risk factors, such as APC resistance (factor V Leiden); a deficiency of protein C, protein S, or antithrombin; or the presence of lupus anticoagulants. After excluding all these subjects (n=141), an unmatched OR for thrombosis of 2.7 (95% CI: 1.3 to 5.6) was found.

Next, the relation between the presence or absence of the 20210 mutation and prothrombin levels was established. Individuals with the normal 20210 GG genotype had a mean prothrombin level of 1.05 U/ml (n=860; SD: 0.15; range: 0.55 to 1.56), whereas individuals with the 20210 AG genotype had a significantly higher mean prothrombin level of 1.32 U/ml (n=40; SD: 0.18; range: 0.95 to 1.78; P <0.001). There was no notable difference in prothrombin levels between patients and control subjects within each of the two genotypic groups. The mean levels (in units per milliliter) of protein C, total protein S, and antithrombin did not differ between the 20210 GG and 20210 AG genotype (1.03, 1.04, and 0.99 v 1.02, 1.03, and 0.98, respectively).

Table 3 shows the distribution of the 20210 genotypes over the different categories of prothrombin activity. Both in patients and control subjects, around 87% of the individuals with the 20210 AG genotype were in the highest category of prothrombin activity (>1.15 U/ml), whereas less notable differences were observed in individuals with the normal 20210 GG genotype.

TABLE 3

Numbers of Individuals With the 20210 GG or AG Genotype for Four Categories of Prothrombin Activity

| | <0.95 | Prothrombin Activity 0.95–1.04 | 1.05–1.15 | >1.15 |
|---|---|---|---|---|
| Patients* (n = 424) | | | | |
| 20210AG | 0 | 1 (3) | 2 (7) | 24 (90) |
| 20210GG | 85 (21) | 105 (26) | 99 (25) | 108 (28) |
| Controls (n = 474) | | | | |
| 20210AG | 0 | 0 | 2 (18) | 9 (82) |
| 20210GG | 134 (29) | 125 (27) | 116 (25) | 88 (19) |
| Total (n = 898) | | | | |
| 20210AG | 0 | 1 (3) | 4 (10) | 33 (87) |
| 20210GG | 219 (25) | 230 (27) | 215 (25) | 196 (23) |

Values are the number of individuals with percentages in parentheses.
*Patients on oral anticoagulant treatment are excluded (n = 48).

The 20210 A allele was not only found to be a risk factor for thrombosis but also to be associated with elevated prothrombin levels. As is shown in example 1, elevated prothrombin levels as such were a risk factor for thrombosis (Table 1). Thus the prothrombin level may be considered as an effector, which automatically means that other factors than the 20210 A allele can be responsible for high prothrombin levels.

FIG. 1 shows the direct sequencing of the G to A transition at position 20210 in the prothrombin gene of a proband with venous thrombosis. The figure shows part of the nucleotide sequence (nt 20198–20229) in one orientation (5' to 3') of the 3'-UT region. The nucleotide differences are indicated by arrows. The sequence of the prothrombin genes of one proband is shown in track 2, and the sequence of the genes of a control subject is shown in track 1.

FIG. 2 gives the strategy for direct detection of the 20210 A allele in the prothrombin gene. A 345-bp fragment form exon 14 and the 3'-UT region of the prothrombin gene was amplified by PCR using the primers 5'-TCTAGAAACAGTTGCCTGGC-3' (pr 93–787, nucleotides 19889–19908) (Biochemistry 26, 6165, 1987) and a mutagenic primer 5'-ATAGCACTGGGAGCATTGAA*GC-3' (pr 95–315, nucleotides 20233–20212) (Biochemistry 26, 6165,1987), as described in example 2. The nucleotide with an asterisk in the mutagenic primer is not present in the normal sequence. A new HindIII site (-A/AGCTT-) is introduced in the amplified fragment from the less-frequent allele (A2:AAG) yielding two fragments (322 bp and 23 bp in length) after enzyme digestion (lane 6). The more frequent allele (A1:GAG) lacks the restriction site and therefore generates only a 345-bp fragment by PCR-HindIII digestion (lanes 1 through 5 and 7). Abbreviation: M, marker.

FIG. 3 shows the pedigree of a family in whom both the 20210 G/A sequence variation in the prothrombin gene and the factor V Leiden mutation (1691 G/A) are segregating. Thrombotic symptoms are indicated by a dotted upper left quartile of the symbols; heterozygosity for the factor V Leiden mutation is indicated by a hatched upper right quartile of the symbols; the presence of the 20210 AA genotype in the prothrombin gene is indicated by a solid lower left and right quartile of the symbols. Individuals tested for the 20210 G/A sequence variation in the prothrombin gene and the factor V Leiden mutation are indicated by a dot to the left of the symbol. The arrow denotes the proposita; individuals indicated by a slash through the symbol are deceased.

We claim:

1. A method for determining whether an individual is at an increased risk for thrombosis, comprising determining the prothrombin level in said individual, whereby an elevated level is indicative of an increased risk for thrombosis.

2. The method according to claim 1, wherein the prothrombin level is assessed by measuring said prothrombin level in a suitable sample and comparing this level with normal prothrombin values.

3. The method according to claim 2, wherein said suitable sample is a blood sample.

4. A method for determining whether an individual is at increased risk for thrombosis, comprising detecting the presence or absence of a genetic mutation that is correlated with elevated prothrombin levels in individuals with the mutation, said elevated prothrombin levels being associated with increased risk for thrombosis.

5. The method according to claim 4, where said genetic mutation is located in the 3'-untranslated region of the prothrombin gene.

6. The method according to claim 5, wherein said mutation is located at nucleotide position 20210.

7. The method according to claim 6, wherein said mutation at nucleotide position 20210 is a G to A transition.

8. The method according to claim 4, wherein the presence or absence of the genetic mutation is determined by performing a nucleic acid amplification reaction.

9. The method according to claim 8, wherein said nucleic acid amplification reaction is carried out using primers which specifically hybridize adjacent to the region of the prothrombin gene that contains the G to A mutation at position 20210, such that a portion of the gene containing the mutation will be amplified.

10. The method according to claim 9, wherein said primers hybridize at or near the 3'-untranslated region of said prothrombin gene.

11. The method according to claim 8, wherein said nucleic acid amplification reaction is an allele specific polymerase chain reaction.

12. The method according to claim 8, wherein amplified nucleic acid products resulting from the reaction are detected by hybridization to a probe.

13. The method according to claim 12, wherein said probe comprises nucleotide 20210 of the prothrombin gene.

14. The method according to claim 8, wherein the amplified nucleic acid products are subjected to sequence analysis.

15. The method according to claim 8, wherein the amplified nucleic acid products are subjected to restriction enzyme digestion.

16. A kit for determining whether an individual is at an increased risk for thrombosis, comprising at least one primer which specifically hybridizes adjacent to the region of the prothrombin gene that contains the G to A mutation at position 20210, and suitable amplification reagents.

17. The kit according to claim 16, wherein said primer hybridizes at or near the 3'-untranslated region of the prothrombin gene.

18. An isolated polynucleotide comprising a mutated prothrombin gene, wherein G at position 20210 is replaced by A, or a fragment of said gene which includes the G to A transition mutation at position 20210.

* * * * *